US012100136B2

(12) United States Patent
Wang

(10) Patent No.: US 12,100,136 B2
(45) Date of Patent: Sep. 24, 2024

(54) NON-CONTACT VITAL SIGN DETECTION DEVICE AND SYSTEM THEREOF

(71) Applicant: MEIZHOU QINGTANG INDUSTRIAL CO, Meizhou (CN)

(72) Inventor: Yuancheng Wang, Meizhou (CN)

(73) Assignee: MEIZHOU QINGTANG INDUSTRIAL CO

( * ) Notice: Subject to any disclaimer, the term of this patent is extended or adjusted under 35 U.S.C. 154(b) by 844 days.

(21) Appl. No.: 17/165,979

(22) Filed: Feb. 3, 2021

(65) Prior Publication Data

US 2021/0166018 A1 Jun. 3, 2021

Related U.S. Application Data

(63) Continuation-in-part of application No. PCT/CN2019/122751, filed on Dec. 3, 2019.

(51) Int. Cl.
| | | |
|---|---|---|
| *G06T 7/00* | (2017.01) | |
| *G02B 27/10* | (2006.01) | |
| *G06V 10/75* | (2022.01) | |
| *G06V 40/18* | (2022.01) | |
| *G06V 40/19* | (2022.01) | |

(52) U.S. Cl.
CPC ........ *G06T 7/0012* (2013.01); *G02B 27/1006* (2013.01); *G06V 10/751* (2022.01); *G06V 40/18* (2022.01); *G06V 40/19* (2022.01); *G06V 40/193* (2022.01); *G06V 40/197* (2022.01); *G06T 2207/30041* (2013.01)

(58) Field of Classification Search
CPC ........ G06T 7/0012; G06T 2207/30041; G02B 27/1006; G06V 10/751; G06V 40/18; G06V 40/19; G06V 40/193; G06V 40/197; A61B 3/14
USPC ........................................................ 351/209
See application file for complete search history.

(56) References Cited

U.S. PATENT DOCUMENTS

2017/0209048 A1* 7/2017 Wiita ..................... A61B 5/202
2022/0354414 A1* 11/2022 Funabiki ................ A61B 3/005
2022/0360706 A1* 11/2022 Ito ........................ A61B 5/4863

FOREIGN PATENT DOCUMENTS

| CN | 101536896 A | 9/2009 |
|---|---|---|
| CN | 101658412 A | 3/2010 |
| CN | 101882222 A | 11/2010 |
| CN | 102429637 A | 5/2012 |
| CN | 105744881 A | 7/2016 |

* cited by examiner

*Primary Examiner* — Mohammed A Hasan
(74) *Attorney, Agent, or Firm* — Jose Cherson Weissbrot

(57) ABSTRACT

The present disclosure provides a non-contact vital sign detection device, which comprises a processing unit, a preset light source, a beam splitter, a camera and a display unit; the processing unit sends an emission instruction to the preset light source and sends a capturing instruction to the camera when detecting a first preset instruction; the preset light source emits a preset light ray outwards when receiving the emission instruction; the beam splitter filters the light ray reflected by the eyes of the target user to the camera based on the preset light ray.

18 Claims, 5 Drawing Sheets

NON-CONTACT VITAL SIGN DETECTION DEVICE AND SYSTEM THEREOF

TECHNICAL FIELD

The present disclosure belongs to the technical field of vital sign detection, and in particular relates to a non-contact vital sign detection device and a system thereof.

BACKGROUND

With the acceleration of population aging and the increase of population in sub-health state, the health awareness of people is increasing day by day, which requires the medical model to change from the traditional mode focusing on symptom treatment to the mode focusing on prevention. At the same time, the development of medical instruments has begun to change from a complex large-scale medical device applied in hospitals to a miniaturized device which is suitable for both hospitals and individuals. The traditional detection method of human health state is to use a contact detection method to detect various indicators of human body with the help of medical instruments. Medical staff can evaluate the health state of users according to the indicators obtained by detection, so as to find out the hidden dangers of health of users in time. However, the existing medical detector has the problems of huge volume, complicated operation process and small application scope, which cannot be applied to ordinary household users lacking professional knowledge.

SUMMARY

Technical Problem

The embodiment of the present disclosure provides a non-contact vital sign detection device and a system thereof, which can solve the problems of the existing medical detector of huge volume, complicated operation process and small application scope, which cannot be applied to ordinary household users lacking professional knowledge.

Technical Solutions

In a first aspect, an embodiment of the present disclosure provides a non-contact vital sign detection device, which comprises a processing unit, a preset light source, a beam splitter, a camera and a display unit; wherein the preset light source, the camera and the display unit are all connected to the processing unit, the preset light source and the camera are provided in the same plane, and the beam splitter is provided in front of the lens of the camera;

the processing unit is configured to send an emission instruction to the preset light source and send a capturing instruction to the camera when detecting a first preset instruction;

the preset light source is configured to emit a preset light ray outwards when receiving the emission instruction; wherein the preset light ray is used for stimulating the iris of a target user;

the beam splitter is configured to filter the light ray reflected by the eyes of the target user to the camera based on the preset light ray;

the camera is configured to capture the eyes of the target user when receiving the capturing instruction and send the captured eye video to the processing unit; wherein the eye video comprises iris information of the target user;

the processing unit is further configured to extract the iris information of the target user from the eye video, compare the iris information of the target user with preset iris information to obtain a first comparison result, and determine a vital sign detection result based on the first comparison result;

the display unit is configured to display the vital sign detection result.

In a second aspect, an embodiment of the present disclosure also provides a non-contact vital sign detection system, which comprises a terminal device and the non-contact vital sign detection device according to the first aspect;

the terminal device is configured to receive the vital sign detection result sent by the non-contact vital sign detection device and display the vital sign detection result.

Beneficial Effects

The non-contact vital sign detection device according to the present disclosure comprises a processing unit, a preset light source, a beam splitter, a camera and a display unit; wherein the preset light source, the camera and the display unit are all connected to the processing unit, the preset light source and the camera are provided in the same plane, and the beam splitter is provided in front of the lens of the camera; the processing unit is configured to send an emission instruction to the preset light source and send a capturing instruction to the camera when detecting a first preset instruction; the preset light source is configured to emit a preset light ray outwards to stimulate the iris of a target user when receiving the emission instruction; the beam splitter is configured to filter the light ray reflected by the eyes of the target user to the camera based on the preset light ray; the camera is configured to capture the eyes of the target user when receiving the capturing instruction and send the captured eye video comprising iris information of the target user to the processing unit; the processing unit is further configured to extract the iris information of the target user from the eye video, compare the iris information of the target user with preset iris information to obtain a first comparison result, and determine a vital sign detection result based on the first comparison result; the display unit is configured to display the vital sign detection result. Therefore, the user only needs to trigger a first preset instruction through the non-contact vital sign detection device and aim the preset light source on the non-contact vital sign detection device at his/her eyes. The non-contact vital sign detection device can automatically detect the health state of the user and display the vital sign detection result for describing the health state of the user. The device is simple to operate, small in size and convenient to carry, and can be applied to ordinary families lacking professional knowledge, and has a wide application scope.

BRIEF DESCRIPTION OF THE DRAWINGS

For a better understanding of the aforementioned embodiments of the invention as well as additional embodiments thereof, reference should be made to the Description of Embodiments below, in conjunction with the following drawings in which like reference numerals refer to corresponding parts throughout the figures.

DETAILED DESCRIPTION

In order to make the object, technical scheme and advantages of the present disclosure clearer, the present disclosure will be further described in detail with reference to the drawings and embodiments. It should be understood that the specific embodiments described herein are only used to explain the present disclosure, rather than limit the present disclosure.

Figure 1:
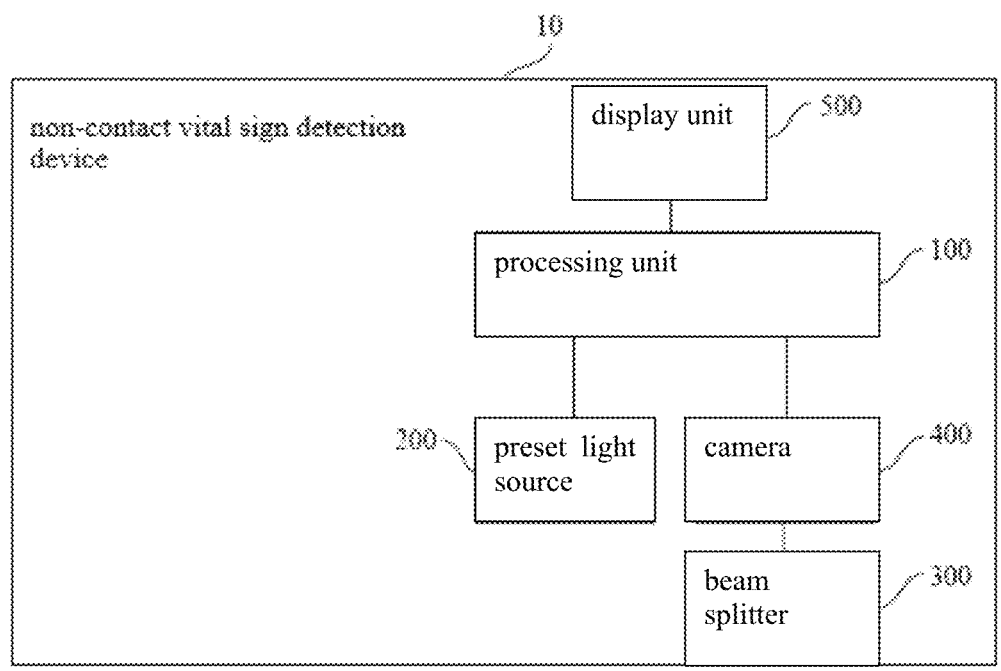
FIG. 1 is a schematic circuit structural diagram of a non-contact vital sign detection device according to an embodiment of the present disclosure.
Figure 2:
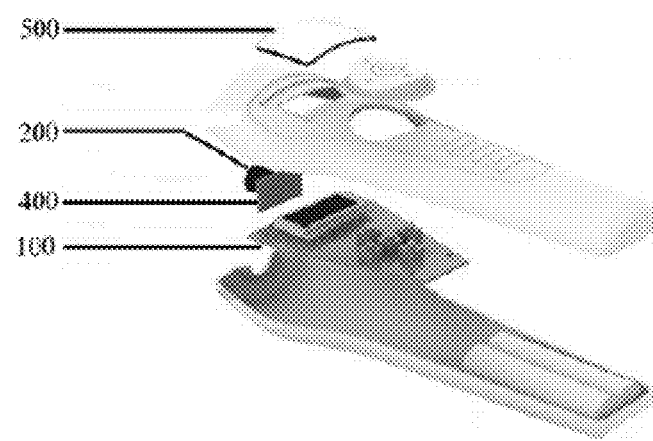
FIG. 2 is a physical structural diagram of a non-contact vital sign detection device according to an embodiment of the present disclosure.

FIG. 1 is a schematic circuit structural diagram of a non-contact vital sign detection device according to the present disclosure, and FIG. 2 is a physical structural diagram of a non-contact vital sign detection device according to an embodiment of the present disclosure. For convenience of explanation, only the parts related to this embodiment are shown and detailed as follows:

As shown in FIGS. 1 and 2, a non-contact vital sign detection device 10 comprises a processing unit 100, a preset light source 200, a beam splitter 300, a camera 400 and a display unit 500. The preset light source 200, the camera 400 and the display unit 500 are all connected to the processing unit 100. The preset light source 200 and the camera 400 are provided in the same plane, and the beam splitter 300 is provided in front of the lens of the camera 400.

The processing unit 100 is configured to send an emission instruction to the preset light source 200 and send a capturing instruction to the camera 400 when the first preset instruction is detected.

The preset light source 200 is configured to emit a preset light ray outwards when receiving the emission instruction; wherein the preset light ray is used for stimulating the iris of a target user.

The beam splitter 300 is configured to filter the light ray reflected by the eyes of the target user to the camera 400 based on the preset light ray.

The camera 400 is configured to capture the eyes of the target user when receiving the capturing instruction and send the captured eye video to the processing unit 100; wherein the eye video comprises iris information of the target user.

The processing unit 100 is further configured to extract the iris information of the target user from the eye video, compare the iris information of the target user with preset iris information to obtain a first comparison result, and determine a vital sign detection result based on the first comparison result.

The display unit 500 is configured to display the vital sign detection result.

In practical application, when a user needs to know his/her health state, he/she can trigger a first preset instruction through the non-contact vital sign detection device 10, and aim the preset light source 200 on the non-contact vital sign detection device 10 at his/her eyes. Wherein the first preset instruction is used to instruct the non-contact vital sign detection device to start detecting the vital sign of the target user. The target user refers to the user who triggers the first preset instruction.

In the embodiment of the present disclosure, the processing unit 100 in the non-contact vital sign detection device 10 sends an emission instruction to the preset light source 200 when detecting the first preset trigger instruction, wherein the emission instruction is used to instruct the preset light source 200 to emit light outwards.

In practical application, a detection button can be set on the non-contact vital sign detection device 10, and the user can trigger the first preset instruction by triggering the detection button. The processing unit 100 detects the first preset instruction, which may be as follows: detecting that the user triggers the detection button. That is, if the processing unit 100 detects that the user has triggered the preset detection button, it is considered that the first preset instruction has been detected.

In the embodiment of the present disclosure, the preset light source 200 emits preset light ray outwards when receiving the emission instruction sent by the processing unit 100. Since the target user aims the preset light source 200 at his/her eyes, the preset light ray emitted by the preset light source 200 will illuminate the eyes of the target user and stimulate the iris of the target user. The eyes of the target user will reflect the preset light ray.

In the embodiment of the present disclosure, in order to obtain iris information of the target user when the preset light irradiates the eyes of the target user, the processing unit 100 sends an emission instruction to the preset light source 200 while sending a capturing instruction to the camera 400, and the capturing instruction instructs the camera 400 to capture the eyes of the target user. It should be noted that in order to avoid the interference of the light ray reflected by the eyes of the target user on the eye video captured by the camera 400, in the embodiment of the present disclosure, the beam splitter 300 is provided in front of the lens of the camera 400, and the beam splitter 300 can filter the light ray reflected by the eyes of the target user, so that the camera 400 can capture high-quality eye video.

The camera 400 starts capturing images when receiving the capturing instruction sent by the processing unit 100. Since the camera 400 and the preset light source 200 are provided in the same plane, when the preset light source 200 is aimed at the eyes of the target user, the camera 400 can capture the eye area of the user, that is, the video captured by the camera 400 is the eye video of the target user. The eye video comprises iris information of the target user.

In practical application, in order to ensure that the camera 400 can capture the eye area of the target user when the user aims the preset light source 200 at the eyes of the target user, the camera 400 can be set close to the preset light source 200, that is, the distance between the camera 400 and the preset light source 200 can be smaller than the preset distance, and the preset distance can be set according to actual needs, which is not limited here.

In practical application, the capturing duration of the camera 400 can be determined according to the irradiation duration of the preset light ray to the eyes of the target user, and the irradiation duration of the preset light ray to the eyes of the target user can be set according to the actual needs, which is not limited here.

In the embodiment of the present disclosure, after capturing the eye video of the target user, the camera 400 sends the eye video to the processing unit 100. After receiving the eye video sent by the camera 400, the processing unit 100 extracts iris information of the target user from the eye video.

It should be noted that the non-contact vital sign detection device 10 further comprises a storage unit (not shown in the figure), in which preset iris information is stored. The preset iris information comprises reference iris information, which is the iris information when the human body is in health state.

After extracting iris information of the target user from the eye video, the processing unit 100 also obtains preset iris information from the storage unit, and compares the iris information of the target user with the preset iris information to obtain a first comparison result. Wherein the first comparison result is used to indicate whether the iris information of the target user is the same as the preset iris information. Specifically, if the iris information of the target user is the same as the preset iris information, the first comparison result is the same. If the iris information of the target user is different from the preset iris information, the first comparison result is different. It should be noted that if the first comparison result is the same, it indicates that the target user is healthy. If the first comparison result is different, it indicates that the target user has health risks.

After obtaining the first comparison result, the processing unit 100 generates the corresponding vital sign detection result according to the first comparison result. Wherein the vital sign detection result is used to describe the health state of the target user. Specifically, if the first comparison result is the same, the generated vital sign detection result may be normal, which indicates that the target user is healthy. If the first comparison result is different, the generated vital sign detection result may be abnormal, which indicates that the target user has health risks.

After obtaining the vital sign detection result, the processing unit 100 sends the vital sign detection result to the display unit 500. The display unit 500 displays the vital sign detection result. For example, if the vital sign detection result is normal, the display unit 500 can display the word "normal", so that the target user knows that he/she is healthy. If the vital sign detection result is abnormal, the display unit 500 can display the word "abnormal", so that the target user knows that he/she has health risks.

In practical application, since the iris of human eyes absorbs different wavelengths of light to a different extent, the images of human eyes obtained when stimulating the iris of the same user with different wavelengths of light are different. In order to improve the accuracy of human vital sign detection, the iris of human eyes can be stimulated with different wavelengths of light, and then the vital sign of users can be comprehensively detected based on the images of human eyes stimulated with different wavelengths of light.

Based on this, as an embodiment of the present disclosure, the preset light source 200 is specifically used to emit preset light rays with different wavelengths outwards when receiving the transmitted emission instruction.

In this embodiment, when receiving the reflection instruction sent by the processing unit 100, the preset light source 200 sequentially emits preset light rays with different wavelengths, wherein the wavelength of the preset light rays can be set according to the actual needs, which is not limited here. The emission sequence and the emission duration of preset light rays with different wavelengths can be set according to actual needs. For example, the emission sequence of preset light rays with different wavelengths can be determined according to the size of wavelengths, and the emission duration of preset light rays with each wavelength can be the same or different. By emitting preset light rays with different wavelengths outwards, the eye video can be captured when the preset light rays with different wavelengths stimulate the eyes of the target user, thus improving the accuracy of vital sign detection.

Figure 9:
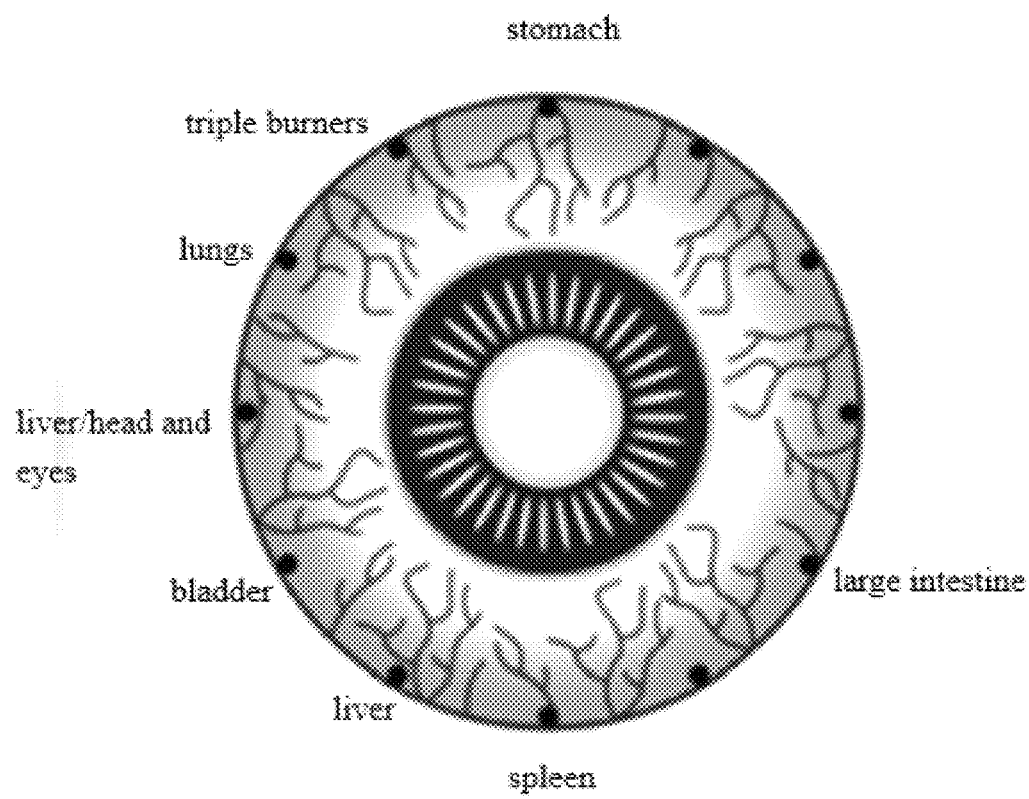
FIG. 9 is a diagram of the corresponding relationship between irises and human organs in a non-contact vital sign detection device according to an embodiment of the present disclosure.

It should be noted that the information of different areas of iris is used to characterize the health state of different organs of human body, that is, different areas of iris correspond to different organs of human body. Specifically, the corresponding relationship between iris and human organs can be shown in FIG. 9.

Based on this, as an embodiment of the present disclosure, the processing unit 100 is further configured to determine an abnormal organ with abnormal index based on the iris information of the target user and the preset iris information if the first comparison result is that the iris information of the target user is different from the preset iris information, and send the identification of the abnormal organ to the display unit 500.

The display unit 500 is further configured to display a preset human organ distribution map and highlight the abnormal organ in the human organ distribution map when receiving the identification of the abnormal organ.

In this embodiment, if it is detected that the iris information of the target user is different from the preset iris information, that is, the first comparison result is different, the processing unit 100 determines the difference between the iris information of the target user and the preset iris information. Since the difference is that the organ corresponding to the area occupied by the iris is an abnormal organ, the processing unit 100 can determine the abnormal organ with abnormal index in the area occupied by the iris based on the difference, and send the identification of the abnormal organ to the display unit 500. In practical application, the identification of the abnormal organ can be the name of the abnormal organ.

In this embodiment, when receiving the identification of the abnormal organ, the display unit 500 displays a preset human organ distribution map and highlights the abnormal organ in the human organ distribution map. For example, highlighting the abnormal organ may be marking the abnormal organ with different colors.

It can be seen from the above that the non-contact vital sign detection device according to the present disclosure comprises a processing unit, a preset light source, a beam splitter, a camera and a display unit; wherein the processing unit is configured to send an emission instruction to the preset light source and send a capturing instruction to the camera when detecting a first preset instruction; the preset light source is configured to emit a preset light ray outwards when receiving the emission instruction; the beam splitter is configured to filter the light ray reflected by the eyes of the target user to the camera based on the preset light ray; the camera is configured to capture the eyes of the target user when receiving the capturing instruction and send the captured eye video to the processing unit; the processing unit is further configured to extract the iris information of the target user from the eye video, compare the iris information of the target user with preset iris information to obtain a first comparison result, and determine a vital sign detection result based on the first comparison result; the display unit is configured to display the vital sign detection result. Therefore, the user only needs to aim the preset light source on the non-contact vital sign detection device at his/her eyes. The non-contact vital sign detection device can automatically output the first comparison result for describing the health state of the user. The device is simple to operate, small in size and convenient to carry, and can be applied to ordinary families lacking professional knowledge, and has a wide application scope.

Figure 3:
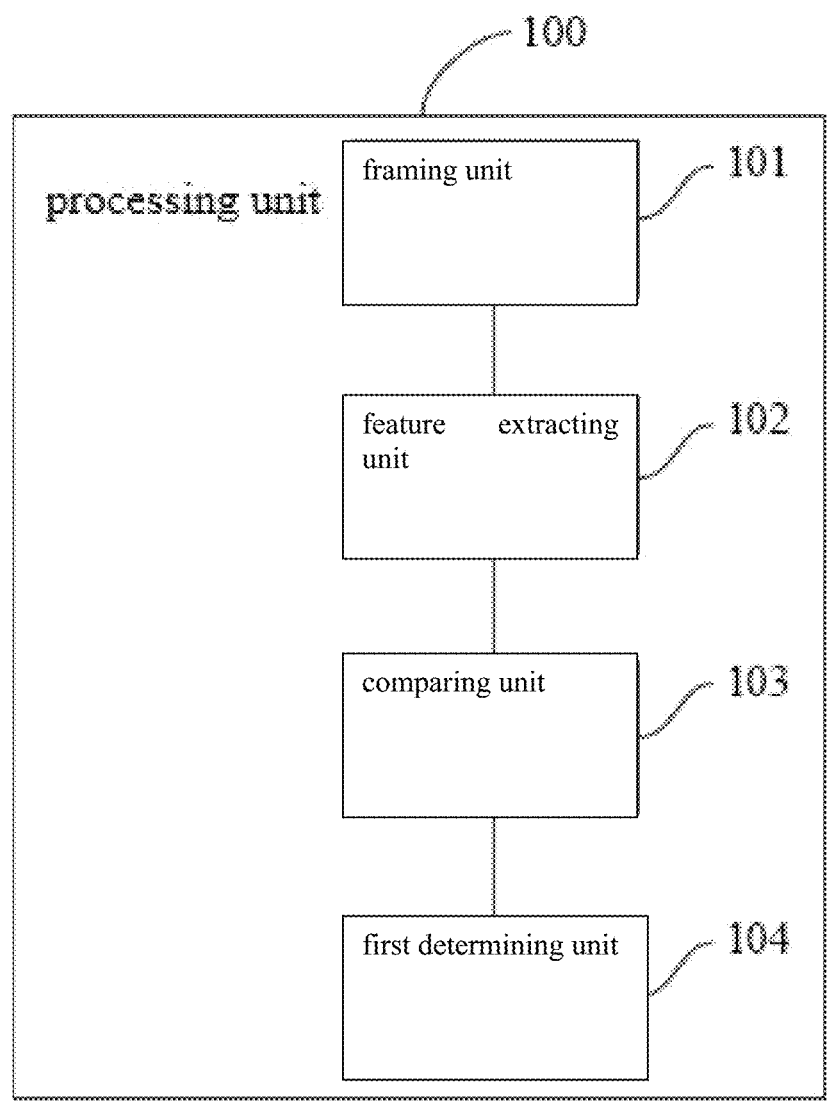
FIG. 3 is a specific structural diagram of a processing unit in a non-contact vital sign detection device according to an embodiment of the present disclosure.

Refer to FIG. 3, which is a specific structural schematic diagram of a processing unit in a non-contact vital sign detection device according to an embodiment of the present disclosure. As shown in FIG. 3, the processing unit 100 in this embodiment comprises:

a framing unit 101, which is configured to frame the eye video to obtain a multi-frame eye image corresponding to the eye video.

a feature extracting unit 102, which is configured to extract the feature value of the iris of the target user from the eye image of each frame.

a comparing unit 103, which is configured to compare each feature value of the iris of the target user with the preset feature value of the iris contained in the preset iris information to obtain a plurality of initial comparison results.

a first determining unit 104, which is configured to determine the first comparison result based on all the initial comparison results.

In this embodiment, after the processing unit 100 receives the eye video of the target user, the framing unit 101 in the processing unit 100 frames the eye video to obtain a multi-frame eye image corresponding to the eye video. In particular, framing refers to dividing the eye video into an image of each frame.

In this embodiment, after obtaining the multi-frame eye image corresponding to the eye video, the framing unit 101 sends the multi-frame eye image to the feature extracting unit 102, and the feature extracting unit 102 extracts the feature value of the iris of the target user from each frame of eye images. In particular, the feature value of iris is represented by a pixel value matrix.

In this embodiment, after extracting a plurality of feature values of the iris of the target user from the multi-frame eye image, the feature extracting unit 102 sends the plurality of feature values of the iris of the target user to the comparing unit 103. The comparing unit 103 compares each feature value of the iris of the target user with the preset feature values of the iris contained in the preset iris information to obtain a plurality of initial comparison results. In particular, the initial comparison results are used to indicate whether a certain feature value of the iris of the target user is the same as the preset feature value. Specifically, if a certain feature value of the iris of the target user is the same as the preset iris feature value, the initial comparison result is the same. If a certain feature value of the iris of the target user is different from the preset iris feature value, the initial comparison result is different.

In this embodiment, after obtaining a plurality of initial comparison results, the comparing unit 103 sends the plurality of initial comparison results to the first determining unit 104, and the first determining unit 104 determines a first comparison result based on all the initial comparison results. Specifically, the first determining unit 104 determines that the first comparison results are the same if it detects that all the initial comparison results are the same, and determines that the first comparison results are different if it detects that at least one of all the initial comparison results is different.

It can be seen from the above that the non-contact vital sign detection device according to this embodiment can improve the accuracy of vital sign detection by considering the iris information in each frame of eye images contained in the eye video and determining the final vital sign detection result through the feature values of irises in all eye images.

Figure 4:
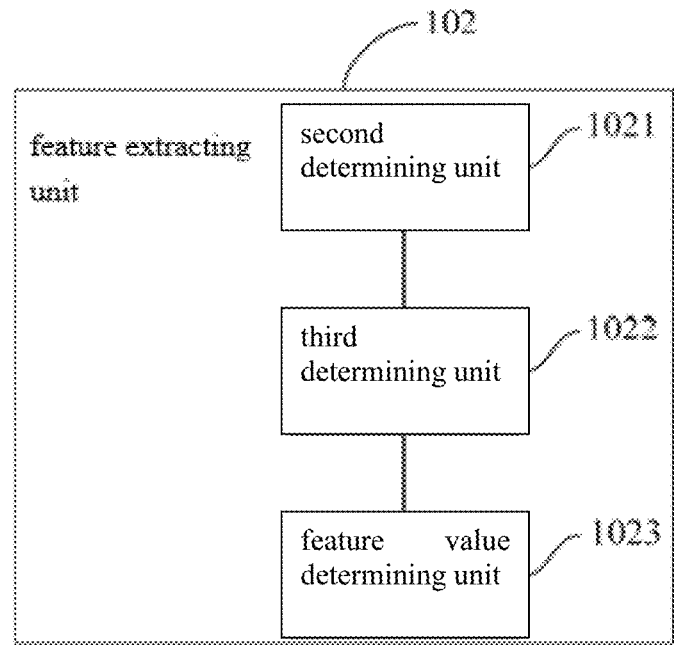
FIG. 4 is a specific structural diagram of a feature extracting unit in a non-contact vital sign detection device according to an embodiment of the present disclosure.

Refer to FIG. 4, which is a specific structural diagram of a feature extracting unit in a non-contact vital sign detection device according to an embodiment of the present disclosure. As shown in FIG. 4, the feature extracting unit 102 in this embodiment specifically comprises:

a second determining unit 1021, which is configured to determine a first circular area occupied by the pupil of the target user in the eye image based on the pixel values of each pixel in the eye image;

a third determining unit 1022, which configured to determine a second circular area in the eye image based on the first circular area and a preset ratio between the iris radius and the pupil radius, and determine a non-overlapping area between the second circular area and the first circular area as an annular area occupied by the iris of the target user in the eye image;

a feature value determining unit 1023, which configured to determine the feature value of the iris of the target user based on pixel values of each pixel in the annular region.

It should be noted that the iris of human eyes is at the forefront of the tunica media oculi and between cornea and crystalline lens, and there is a round hole in the center of iris, which is referred to as pupil. Generally, people of different races have different colors of iris, but the colors of pupils are the same, usually black. The iris radius and the pupil radius of people are usually fixed, that is, the ratio of the iris radius to the pupil radius is fixed, and the ratio of the iris radius to the pupil radius can be obtained according to actual measurement.

Since the colors of human pupils are all black, in this embodiment, the second determining unit 1021 may first determine the first circular area occupied by the pupil of the target user in the eye image based on the pixel values of each pixel in the eye image. Specifically, since the pixel with the pixel value of 0 is displayed as black, the second determining unit 1021 may determine the area formed by all pixels with the pixel value of 0 in the eye image as the first circular area occupied by the pupil of the target user in the eye image.

Since the pupil is located in the center of iris, that is, the pupil and iris are concentric, after the second determining unit 1021 determines the first circular area occupied by the pupil of the target user in the eye image, the third determining unit 1022 can determine the second circular area in the eye image based on the first circular area and the preset ratio between the iris radius and the pupil radius, and determine the non-overlapping area between the second circular area and the first circular area as the annular area occupied by the iris of the target user in the eye image.

After the third determining unit 1022 determines the annular area occupied by the iris of the target user in the eye image, the feature value determining unit 1023 determines the feature value of the iris of the target user based on the pixel values of each pixel in the annular area. Specifically, the pixel value set formed by the pixel values of all pixels in the annular area is the feature value of the iris.

It can be seen from the above that the non-contact vital sign detection device according to this embodiment first determines the position of the pupil by the pixel value of each pixel in the eye image, and then determines the area occupied by the iris based on the ratio of the iris radius and the pupil radius, thereby accurately extracting the feature value of the iris from the eye image and improving the accuracy of vital sign detection.

Figure 5:
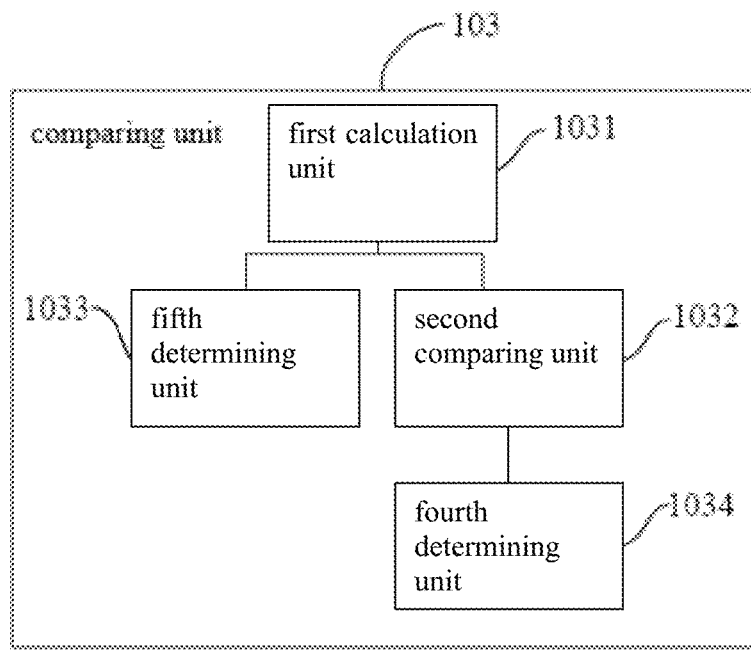
FIG. 5 is a specific structural diagram of a comparing unit in a non-contact vital sign detection device according to an embodiment of the present disclosure.

Refer to FIG. 5, which is a specific structural diagram of a comparing unit in a non-contact vital sign detection device according to an embodiment of the present disclosure. As shown in FIG. 5, the comparing unit 103 in this embodiment specifically comprises:

a first calculation unit 1031, which is configured to calculate a first difference between each feature value of the iris of the target user and a first preset feature value of the iris contained in the reference iris information;

a second comparing unit 1032, which is configured to determine a first target feature value in which the first difference with the first preset feature value is larger than a first preset difference threshold from all the feature values of the iris of the target user, and compare each first target feature value with a second preset feature value of the iris contained in each abnormal iris information to obtain a plurality of second comparison results corresponding to each first target feature value;

a fourth determining unit 1033, which is configured to determine the initial comparison result corresponding to each of the feature values based on all the second comparison results corresponding to each of the first target feature values;

a fifth determining unit 1034, which is configured to determine a second target feature value in which the first difference with the first preset feature value is less than or equal to the first preset difference threshold from all the feature values of the iris of the target user, and determine that the initial comparison results corresponding to all the second target feature values are the same.

It should be noted that in this embodiment, the preset iris information comprises reference iris information and a plurality of pieces of abnormal iris information. Wherein, each piece of abnormal iris information is used to describe the iris information of a user when an organ of the user is abnormal.

After the comparing unit 103 receives the feature value of the iris of the target user, the first calculation unit 1031 in the comparing unit 103 calculates the first difference between each feature value of the iris of the target user and the first preset feature value of the iris contained in the reference iris information.

After obtaining a plurality of first differences, the first calculation unit 1031 sends the first differences to the second comparing unit 1032 and the fifth determining unit 1034.

The second comparing unit 1032 compares each first difference with the first preset difference threshold, and if at least one first difference is detected to be greater than the first preset difference threshold, it indicates that there is a great difference between the iris information of the target user and the reference iris information, that is, the target user may have health risks. At this time, it is necessary to compare the iris information of the target user which has a great difference with the reference iris information with the abnormal iris information, so as to determine whether each organ of the target user is abnormal. Specifically, the second comparing unit 1032 determines the first target feature value in which a first difference with the first preset feature value is larger than a first preset difference threshold from all the feature values of the iris of the target user, and compares each first target feature value with a second preset feature value of the iris contained in each abnormal iris information to obtain a plurality of second comparison results corresponding to each first target feature value.

In particular, the second comparison result is used to indicate whether the first target feature value of the iris of the target user is the same as the second preset feature value. Specifically, if the first target feature value of the iris of the target user is the same as the second preset iris feature value, the second comparison result is the same. If the first target feature value of the iris of the target user is different from the second preset iris feature value, the second comparison result is different.

It should be noted that if the second comparison result is the same, it indicates that the first target feature value of the iris of the target user is the same as the second preset iris feature value, indicating that the iris information of the target user is the same as the abnormal iris information. Furthermore, because the abnormal iris information represents the iris information when an organ is abnormal, it can be determined that the organ of the target user is abnormal. If the second comparison result is different, it indicates that the first target feature value of the iris of the target user is different from the second preset iris feature value, indicating that the iris information of the target user is different from the abnormal iris information. Furthermore, because the abnormal iris information represents the iris information when an organ is abnormal, it can be determined that the organ of the target user is normal.

In this embodiment, after receiving a plurality of second comparison results sent by the second comparing unit 1032, the fourth determining unit 1033 determines the initial comparison result corresponding to each feature value based on all the second comparison results corresponding to each first target feature value. It should be noted that the fourth determining unit 1033 determines that the initial comparison results are the same if it is detected that all the second comparison results are different, and determines that the initial comparison results are different if it is detected that at least one second comparison result is the same.

In this embodiment, after receiving a plurality of first differences, the fifth determining unit 1034 determines the second target feature value in which a first difference with the first preset feature value is less than or equal to the first preset difference threshold from all the feature values of the iris of the target user, because if it is detected that all the first differences are less than or equal to the first preset difference threshold, it indicates that the iris information of the target user is consistent with the reference iris information, and it is determined that the initial comparison results corresponding to all the second target feature values are the same.

It can be seen from the above that the non-contact vital sign detection device according to this embodiment can further compare the first target feature value with larger difference with the second preset feature value of abnormal iris information when it is detected that there is a large difference between the feature value of the iris of the target user and the first preset feature value of the reference iris information, and further confirm whether the target user has an abnormal organ, thus improving the accuracy of vital sign detection.

Figure 6:
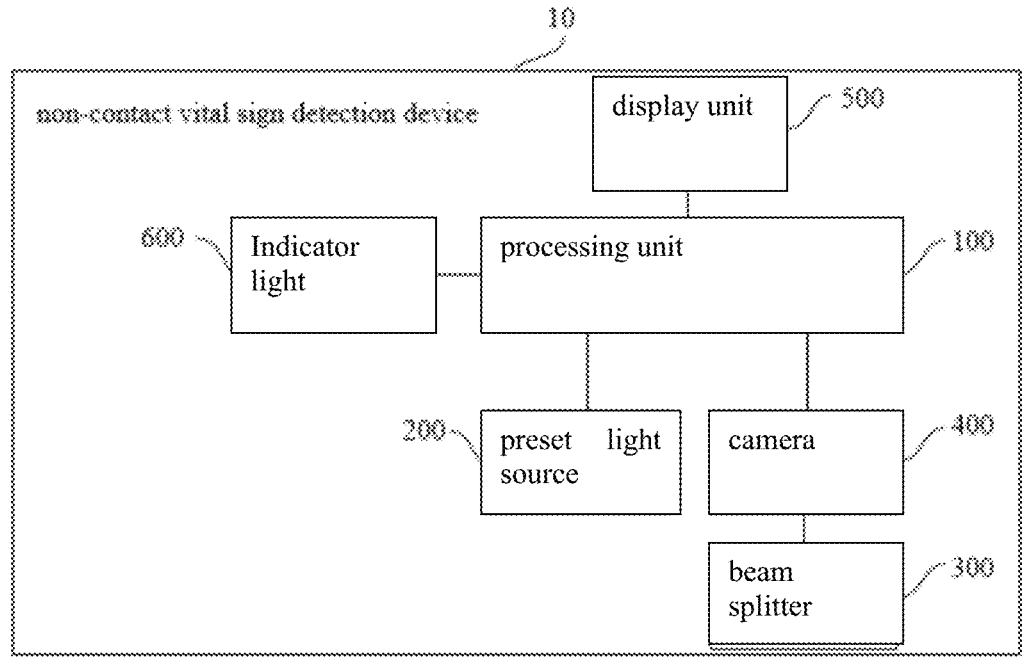
FIG. 6 is a schematic circuit structural diagram of a non-contact vital sign detection device according to another embodiment of the present disclosure.

FIG. 6 is a schematic circuit structural diagram of a non-contact vital sign detection device according to another embodiment of the present disclosure. As shown in FIG. 6, compared with the corresponding embodiment of FIG. 1, the non-contact vital sign detection device 10 in this embodiment further comprises an indicator light 600; the indicator light 600 is connected to the processing unit 100.

In this embodiment, the processing unit 100 is further configured to send a first indication instruction to the indicator light 600 if it is detected that the vital sign detection result is normal; and send a second indication instruction to the indicator light 600 if it is detected that the vital sign detection result is abnormal.

The indicator light 600 is configured to display a first preset color when receiving the first indication instruction; and display a second preset color when receiving the second instruction.

In this embodiment, the first preset color should be different from the second preset color. The first preset color and the second preset color can be set according to actual needs. For example, the first preset color can be green and the second preset color can be red. When the indicator light 600 displays the first preset color, it indicates that the vital sign detection result of the target user is normal. When the indicator light 600 displays the second preset color, it indicates that the vital sign detection result of the target user is abnormal.

It can be seen from the above that the non-contact vital sign detection device according to this embodiment can indicate the vital sign detection result of the target user through the indicator light, and can intuitively feed the vital sign detection result of the target user back to the target user, so that the user can know the vital sign detection result more conveniently.

Figure 7:
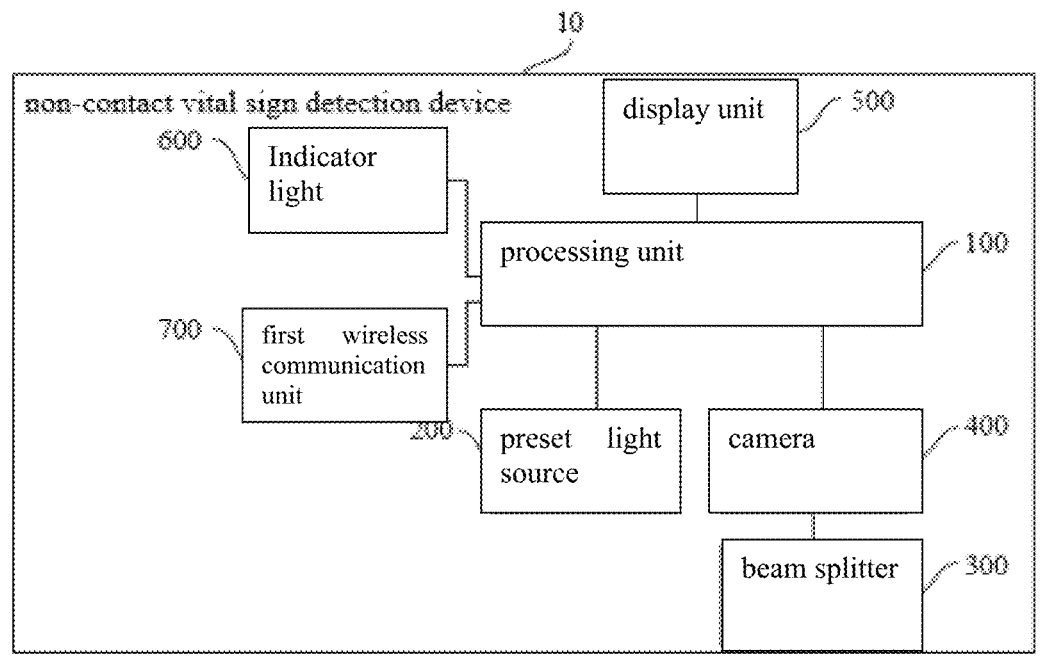
FIG. 7 is a schematic circuit structural diagram of a non-contact vital sign detection device according to another embodiment of the present disclosure.

FIG. 7 is a schematic circuit structural diagram of a non-contact vital sign detection device according to another embodiment of the present disclosure. As shown in FIG. 7, compared with the embodiments corresponding to FIGS. 1 to 6, the non-contact vital sign detection device 10 in this embodiment further comprises a first wireless communication unit 700; the first wireless communication unit 700 is connected to the processing unit 100.

In this embodiment, the processing unit 100 is further configured to send the vital sign detection result to the first wireless communication unit 700.

The first wireless communication unit 700 is configured to send the vital sign detection result to a terminal device wirelessly connected to the non-contact vital sign detection device.

In this embodiment, the terminal device can be set according to actual needs. For example, the terminal device can be a desktop computer, a tablet computer and/or a mobile phone and so on.

It can be seen from the above that the non-contact vital sign detection device according to this embodiment can send the vital sign detection result of the target user to the terminal device wirelessly connected therewith by providing the first wireless communication unit, so that the vital sign detection result of the target user can be sent to the terminal device of the guardian when necessary, which is convenient for the guardian of the target user to understand the vital sign detection result.

Figure 8:
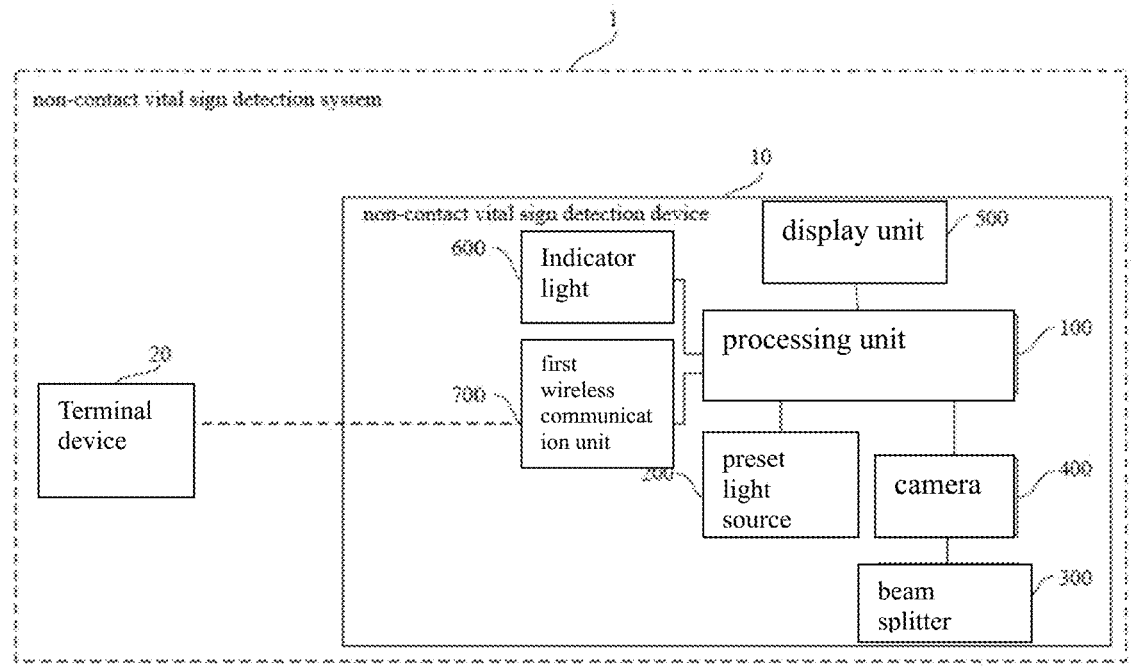
FIG. 8 is a structural schematic diagram of a non-contact vital sign detection system according to an embodiment of the present disclosure.

The embodiment of the present disclosure further provides a non-contact vital sign detection system. FIG. 8 is a structural schematic diagram of a non-contact vital sign detection system according to the embodiment of the present disclosure. As shown in FIG. 8, a non-contact vital sign detection system 1 comprises a terminal device 20 and the non-contact vital sign detection device 10 according to the above embodiment.

The terminal device 20 is configured to receive the vital sign detection result sent by the non-contact vital sign detection device 10 and display the vital sign detection result.

Specifically, the terminal device 20 may comprise a second wireless communication unit (not shown in the figure). When the vital sign detection result needs to be sent to the terminal device 20, the non-contact vital sign detection device 10 may establish a communication connection with the second wireless communication unit in the terminal device 20 through the first wireless communication unit, and then send the vital sign detection result to the terminal device 20 through the first wireless communication unit.

It can be seen from the above that the non-contact vital sign detection system according to this embodiment comprises a non-contact vital sign detection device and a terminal device;

the terminal device is configured to receive the vital sign detection results sent by the non-contact vital sign detection device and display the vital sign detection results, so that the users can view their own vital sign detection reports at any time.

The above is only an optional embodiment of the present disclosure, and is not used to limit the present disclosure. For those skilled in the art, various modifications and variations of the present disclosure are possible. Any modification, equivalent substitution, improvement, etc. made within the spirit and principle of the present disclosure shall be included within the scope of the claims of the present disclosure.

What is claimed is:

1. A non-contact vital sign detection device comprising a processing unit, a preset light source, a beam splitter, a camera and a display unit, wherein the preset light source, the camera and the display unit are all connected to the processing unit, the preset light source and the camera are provided in the same plane, and the beam splitter is provided in front of a lens of the camera;
the processing unit is configured to send an emission instruction to the preset light source and send a capturing instruction to the camera when a first preset instruction is detected;
the preset light source is configured to emit a preset light ray outwards when the emission instruction is received, wherein the preset light ray is used for stimulating an iris of a target user;
the beam splitter is configured to filter the preset light ray reflected by eyes of the target user to the camera;
the camera is configured to capture the eyes of the target user when the capturing instruction is received, and send a captured eye video to the processing unit, wherein the eye video comprises iris information of the target user;
the processing unit is further configured to extract the iris information of the target user from the eye video, compare the iris information of the target user with preset iris information to obtain a first comparison result, and determine a vital sign detection result based on the first comparison result;
the display unit is configured to display the vital sign detection result.

2. The non-contact vital sign detection device of claim 1, wherein the iris information comprises a feature value of the iris and the processing unit comprises:
a framing unit, which is configured to frame the eye video to obtain a multi-frame eye image corresponding to the eye video;

a feature extracting unit, which is configured to extract the feature value of the iris of the target user from the eye image of each frame;

a comparing unit, which is configured to compare each feature value of the iris of the target user with the preset feature value of the iris contained in the preset iris information to obtain a plurality of initial comparison results;

a first determining unit, which is configured to determine the first comparison result based on all the initial comparison results.

3. The non-contact vital sign detection device of claim 2, wherein the feature extracting unit comprises:

a second determining unit, which is configured to determine a first circular area occupied by the pupil of the target user in the eye image based on the pixel values of each pixel in the eye image;

a third determining unit, which configured to determine a second circular area in the eye image based on the first circular area and a preset ratio between the iris radius and the pupil radius, and determine a non-overlapping area between the second circular area and the first circular area as an annular area occupied by the iris of the target user in the eye image;

a feature value determining unit, which configured to determine the feature value of the iris of the target user based on pixel values of each pixel in the annular region.

4. The non-contact vital sign detection device of claim 2, wherein the preset iris information comprises reference iris information and a plurality of pieces of abnormal iris information and the comparing unit comprises: a first calculation unit, which is configured to calculate a first difference between each feature value of the iris of the target user and a first preset feature value of the iris contained in the reference iris information; a second comparing unit, which is configured to determine a first target feature value in which the first difference with the first preset feature value is larger than a first preset difference threshold from all the feature values of the iris of the target user, and compare each first target feature value with a second preset feature value of the iris contained in each abnormal iris information to obtain a plurality of second comparison results corresponding to each first target feature value; a fourth determining unit, which is configured to determine the initial comparison result corresponding to each of the feature values based on all the second comparison results corresponding to each of the first target feature values.

5. The non-contact vital sign detection device of claim 4, wherein the comparing unit comprises:

a fifth determining unit, which is configured to determine a second target feature value in which the first difference with the first preset feature value is less than or equal to the first preset difference threshold from all the feature values of the iris of the target user, and determine that the initial comparison results corresponding to all the second target feature values are the same.

6. The non-contact vital sign detection device of claim 1, wherein the preset light source is configured to emit the preset light ray with different wavelengths outwards when receiving the emission instruction.

7. The non-contact vital sign detection device of claim 1, wherein the processing unit is further configured to determine an abnormal organ with abnormal index based on the iris information of the target user and the preset iris information if the first comparison result is that the iris information of the target user is different from the preset iris information, and send the identification of the abnormal organ to the display unit;

the display unit is further configured to display a preset human organ distribution map and highlight the abnormal organ in the human organ distribution map when receiving the identification of the abnormal organ.

8. The non-contact vital sign detection device of claim 1, wherein the non-contact vital sign detection device further comprises an indicator light and the indicator light is connected to the processing unit;

the processing unit is further configured to send a first indication instruction to the indicator light if it is detected that the vital sign detection result is normal; and send a second indication instruction to the indicator light if it is detected that the vital sign detection result is abnormal;

the indicator light is configured to display a first preset color when receiving the first indication instruction; and display a second preset color when receiving the second instruction.

9. The non-contact vital sign detection device of claim 1, wherein the non-contact vital sign detection device comprises a first wireless communication unit and the first wireless communication unit is connected to the processing unit;

the processing unit is further configured to send the vital sign detection result to the first wireless communication unit;

the first wireless communication unit is configured to send the vital sign detection result to the terminal device wirelessly connected to the non-contact vital sign detection device.

10. A non-contact vital sign detection system comprising a terminal device and a non-contact vital sign detection device;

wherein the non-contact vital sign detection device comprising a processing unit, a preset light source, a beam splitter, a camera, a display unit and a first wireless communication unit, wherein the preset light source, the camera, the display unit and the first wireless communication unit are all connected to the processing unit, the preset light source and the camera are provided in the same plane, and the beam splitter is provided in front of the lens of the camera;

the processing unit is configured to send an emission instruction to the preset light source and send a capturing instruction to the camera when detecting a first preset instruction;

the preset light source is configured to emit a preset light ray outwards when receiving the emission instruction; wherein the preset light ray is used for stimulating the iris of a target user;

the beam splitter is configured to filter the light ray reflected by the eyes of the target user to the camera based on the preset light ray;

the camera is configured to capture the eyes of the target user when receiving the capturing instruction and send a captured eye video to the processing unit; wherein the eye video comprises iris information of the target user;

the processing unit is further configured to extract the iris information of the target user from the eye video, compare the iris information of the target user with preset iris information to obtain a first comparison result, and determine a vital sign detection result based on the first comparison result;

the display unit is configured to display the vital sign detection result;

the processing unit is further configured to send the vital sign detection result to the first wireless communication unit;

the first wireless communication unit is configured to send the vital sign detection result to the terminal device wirelessly connected to the non-contact vital sign detection device;

the terminal device is configured to receive the vital sign detection result sent by the non-contact vital sign detection device and display the vital sign detection result.

11. The non-contact vital sign detection system of claim 10, wherein the iris information comprises a feature value of the iris and the processing unit specifically comprises:

a framing unit, which is configured to frame the eye video to obtain a multi-frame eye image corresponding to the eye video;

a feature extracting unit, which is configured to extract the feature value of the iris of the target user from the eye image of each frame;

a comparing unit, which is configured to compare each feature value of the iris of the target user with the preset feature value of the iris contained in the preset iris information to obtain a plurality of initial comparison results;

a first determining unit, which is configured to determine the first comparison result based on all the initial comparison results.

12. The non-contact vital sign detection system of claim 11, wherein the feature extracting unit comprises:

a second determining unit, which is configured to determine a first circular area occupied by the pupil of the target user in the eye image based on the pixel values of each pixel in the eye image;

a third determining unit, which configured to determine a second circular area in the eye image based on the first circular area and a preset ratio between the iris radius and the pupil radius, and determine a non-overlapping area between the second circular area and the first circular area as an annular area occupied by the iris of the target user in the eye image;

a feature value determining unit, which configured to determine the feature value of the iris of the target user based on pixel values of each pixel in the annular region.

13. The non-contact vital sign detection system of claim 11, wherein the preset iris information comprises reference iris information and a plurality of pieces of abnormal iris information and the comparing unit comprises: a first calculation unit, which is configured to calculate a first difference between each feature value of the iris of the target user and a first preset feature value of the iris contained in the reference iris information; a second comparing unit, which is configured to determine a first target feature value in which the first difference with the first preset feature value is larger than a first preset difference threshold from all the feature values of the iris of the target user, and compare each first target feature value with a second preset feature value of the iris contained in each abnormal iris information to obtain a plurality of second comparison results corresponding to each first target feature value; a fourth determining unit, which is configured to determine the initial comparison result corresponding to each of the feature values based on all the second comparison results corresponding to each of the first target feature values.

14. The non-contact vital sign detection system of claim 13, wherein the comparing unit comprises:

a fifth determining unit, which is configured to determine a second target feature value in which the first difference with the first preset feature value is less than or equal to the first preset difference threshold from all the feature values of the iris of the target user, and determine that the initial comparison results corresponding to all the second target feature values are the same.

15. The non-contact vital sign detection system of claim 10, wherein the preset light source is configured to emit the preset light ray with different wavelengths outwards when receiving the emission instruction.

16. The non-contact vital sign detection system of claim 10, wherein the processing unit is further configured to determine an abnormal organ with abnormal index based on the iris information of the target user and the preset iris information if the first comparison result is that the iris information of the target user is different from the preset iris information, and send the identification of the abnormal organ to the display unit;

the display unit is further configured to display a preset human organ distribution map and highlight the abnormal organ in the human organ distribution map when receiving the identification of the abnormal organ.

17. The non-contact vital sign detection system of claim 10, wherein the non-contact vital sign detection device further comprises an indicator light and the indicator light is connected to the processing unit;

the processing unit is further configured to send a first indication instruction to the indicator light if it is detected that the vital sign detection result is normal; and send a second indication instruction to the indicator light if it is detected that the vital sign detection result is abnormal;

the indicator light is configured to display a first preset color when receiving the first indication instruction; and display a second preset color when receiving the second instruction.

18. The non-contact vital sign detection system of claim 10, wherein the terminal device comprise a second wireless communication unit;

the second wireless communication unit is configured to receive the vital sign detection result sent by the first wireless communication unit.

* * * * *